United States Patent [19]

Hartley et al.

[11] 4,403,036

[45] Sep. 6, 1983

[54] GENETIC REAGENTS FOR GENERATING PLASMIDS CONTAINING MULTIPLE COPIES OF DNA SEGMENTS

[75] Inventors: James L. Hartley; Tamara J. Gregori, both of Iowa City, Iowa

[73] Assignee: University of Iowa Research Foundation, Iowa City, Iowa

[21] Appl. No.: 212,254

[22] Filed: Dec. 2, 1980

[51] Int. Cl.³ .................. C12N 1/00; C12P 21/00; C12P 21/04; C12P 19/34
[52] U.S. Cl. .................... 435/317; 435/68; 435/70; 435/91
[58] Field of Search .............. 435/172, 317, 68, 70, 435/91; 536/27

[56] References Cited

U.S. PATENT DOCUMENTS 4,293,652 10/1981 Cohen ................... 435/91

OTHER PUBLICATIONS

Sadler et al., Gene, 3, 211–232 (1978).
Sadler et al., Gene, 8, 279–300 (1980).
Lewin; *Gene Expression*-3, John Wiley & Sons, New York, 1977, p. 291.
Roberts; Methods in Enzymol. 68, 27 (1979).
Hohn; Methods in Enzymol. 68, 299 (1979).
Bolivar et al.: Gene 2, 95 (1977).

*Primary Examiner*—Thomas G. Wiseman
*Assistant Examiner*—James Martinell

[57] ABSTRACT

Genetic reagents for generating plasmids containing multiples of a DNA segment are prepared by modification of the restriction sites of plasmid rings. The modified plasmids permit cloning of DNA segments which can be recovered with sticky ends that are complementary but not rotationally equivalent. Such segments will polymerize in a head-to-tail conformation. The plasmid rings with modified restriction sites are also used in linear form to obtain head-to-tail joining of multiple DNA segments into plasmid rings for further cloning and/or expression of the DNA segment-directed protein. The critical restriction site sequences of the modified plasmid rings can be prepared as a reagent which permits the sequence to be introduced into any plasmid. The reagents have utility in preparing multiples of protein-forming genes, and in preparing large amounts of homogeneous DNAs which can themselves be used as reagents.

5 Claims, 11 Drawing Figures pARA REAGENT pARA REAGENT pARA REAGENT

POLYMERIZABLE DNA SEGMENT pARA REAGENT

POLIN REAGENT

PLASMID WITH
MULTIPLE DNA SEGMENTS

RESTRICTION SITE REAGENT

RESTRICTION SITE REAGENT

GENETIC REAGENTS FOR GENERATING PLASMIDS CONTAINING MULTIPLE COPIES OF DNA SEGMENTS

BACKGROUND AND PRIOR ART

The field of this invention relates to the introduction of DNA segments, which may be genes, into bacterial plasmids, and the use of the resulting recombinant plasmids for bacterial cloning of the plasmids and/or expression of the proteins directed by the recombinant DNAs. In particular, this invention is concerned with the preparation of plasmids containing many tandem copies of a selected DNA segment. Since genes produce their products (proteins) in approximate proportion to their number (see, for example, S. Normark, et al, *J. Bacteriol.* 132, 912922, 1977), plasmids containing many copies of a protein gene can be used to cause bacteria to make that protein in large quantities. This invention is thus an extension of recombinant DNA technology. In addition, the multiple copies of the DNA segments have commercial value in themselves, for example as reagents for recombinant DNA processes.

J. R. Sadler and colleagues (Sadler, et al, Gene, 3, 211–232, 1978) were able to prepare from the plasmid pMB9 recombinant plasmids containing from one to four tandem repeats of a synthetic lac operator. (An operator in this context is a DNA segment which controls the expression of a gene.) Later attempts by Sadler and his associates to prepare plasmids containing larger numbers of copies of the operator employed the plasmids containing four operators as starting material (Sadler, et al, Gene, 8, 279–300, 1980). By a laborious procedure they were able to prepare a plasmid containing 12 lac operators. One serious problem was the in vivo instability of the plasmids containing multiple operators. It was reported that a primary cause of the instability was believed to be inverted orientations of some of the operator segments in the recombinant plasmids. Such inversions in plasmids containing three or more operators were said to lead to rapid reduction, in vivo of the number of operators, usually to 1 or 2 operators.

With reference to the work of Sadler, et al, which is believed to represent the state of the art in this field, there is a clear need for simpler and more direct procedures for preparing plasmids containing multiple copies of DNA segments, and particularly for plasmids with the repeated sequences arranged uniformly in head-to-tail conformation without segment inversions causing in vivo instability.

SUMMARY OF INVENTION

The present invention relates to a series of interrelated genetic reagents for preparing bacterial plasmids containing multiples of a selected DNA segment with the segments arranged in head-to-tail conformation. The key reagent is prepared by modification of the restriction sites of natural plasmid rings such as the plasmid pBR322. Preferably, the plasmid is selected so that it has a single non-symmetric cleavage site for a restriction endonuclease, the site being denoted S1, which generates sticky ends (i.e., protruding 5' termini) upon cleavage. These ends are not rotationally equivalent due to the non-symmetry of the cleavage site. An example of such an enzyme is Ava I, one cleavage site of which is the sequence 5'-CTCGGG-3' and its complement. The plasmid ring is cut at this site with the appropriate restriction endonuclease, the sticky ends are filled in to provide partial S1 sites at each end of the linear DNA, and the ends are ligated back together through a DNA linker molecule which provides a second restriction site, denoted S2. The linker is chosen such that its terminal base pairs reconstitute the S1 sites, as well as providing the new S2 site. Preferably S2 is a restriction site not otherwise present in the reformed plasmid. For example, if an EcoR I linker is to be used, any EcoR I site already present can be removed from the plasmid before it is initially cut with the enzyme recognizing and cleaning the S1 site.

The reformed plasmid containing the sequence of the three restriction sites with the S1 sites on both sides of the restriction site linker comprises the primary reagent for purpose of the present invention, and is referred to herein as pARA. As will subsequently be described in greater detail, pARA can be employed for cloning DNA segments, which following cloning can be recovered as separated segments with rotationally non-equivalent sticky ends. The resulting cloned and excised DNA segments will then polymerize almost exclusively in head-to-tail conformation, The pARA reagent is also employed to prepare a linear initiator for polymerization of tandem repeats of the cloned DNA segments. For this purpose, pARA is cut with the restriction enzyme for the S1 site to yield the plasmid DNA in linear form with non-equivalent sticky ends. One of the ends is filled in to provide a blunt or flush end and this end is blocked or partially blocked, by eliminating either the terminal 3'-OH group, the 5'-P group, or both. The other end is not changed, except for the removal of the 5'-P if the 5'-P on the blocked end was removed. In either case, the non-blocked end remains as a sticky end. This pARA-derived polymerization initiator reagent is referred to herein as POLIN. By causing the cloned DNA segments with the non-equivalent sticky ends to undergo polymerization in the presence of POLIN, head-to-tail repeats of the DNA segments are joined onto the sticky end of POLIN. Since some of the DNA segments through self-polymerization may circularize on themselves, and thereby become unavailable for ligation to POLIN, it is preferable to introduce the polymerizable segments repeatedly as the polymerization reaction proceeds. After the polymerization has proceeded to the desired extent, the sticky ends of the terminal DNA segments are filled in to provide linear DNA chains with both ends blunt, the 5'-P groups are replaced if they have been removed during blocking, and the linear DNAs are ligated to circular form. The resulting plasmids contain multiples of the DNA segment with each segment arranged in the same conformation, i.e., in head-to-tail fashion. These plasmids can then be transformed into suitable bacteria, such as Escherichia coli, for use in cloning the plasmid or for expression of the protein, as directed by the multiple DNA segments.

THE DRAWINGS

The accompanying drawings will assist in providing an understanding of the structure of the genetic reagents of this invention.

FIG. 1 is a representation of a pARA modified plasmid. This example of pARA contains a three restriction site sequence with the first and third nonsymmetric sites being Ava I sites, which are linked by a different restriction site, denoted S2, which is not found elsewhere in the plasmid ring.

FIG. 2 is a partial view of the pARA reagent of FIG. 1 showing the arrangement of the base pairs in the EcorR I (S2) linker. The guanine-cytosine base pair on the left end of the linker provides the final base pair of the left Ava I site, and is thus required to reconstitute the left Ava I site. Similarly, the final cytosine-guanine base pair on the right end of the linker is required to reform the right Ava I site.

Figure 6:
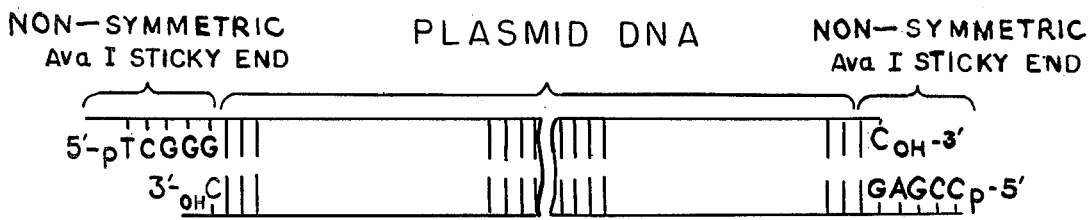
FIG. 6 illustrates the form of the pARA reagent of FIG. 1 after Ava I enzyme cleavage.
Figure 7:
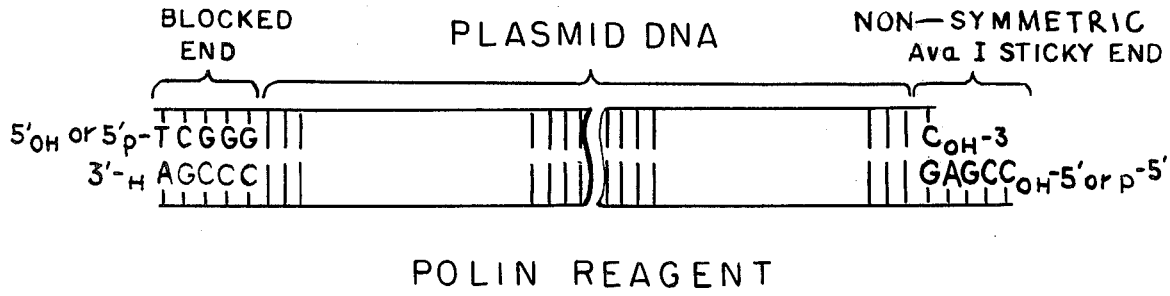

FIG. 7 illustrates the structure of a POLIN reagent formed from the cleaved pARA of FIG. 6. One of the Ava I sticky ends has been filled to provide a blunt end and either the 5'-phosphate or the 3'-hydroxyl group or both have been modified so that the end is blocked from joining to any other terminus. The other end of POLIN retains its AVA I sticky end configuration.

Figure 4:
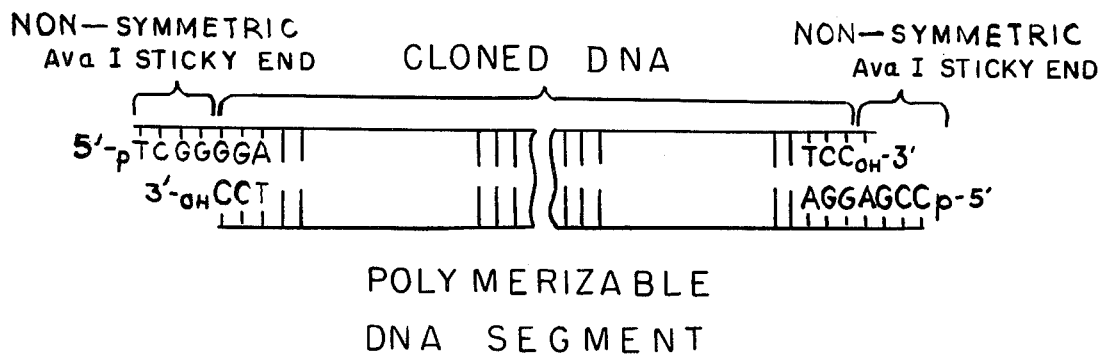
FIG. 4 illustrates the polymerizable DNA segment obtained by separation of the cloned DNA segment from the plasmid rings with the Ava I endonuclease, the cloned DNA segment thereby being provided with non-equivalent Ava I sticky ends.
Figure 8:
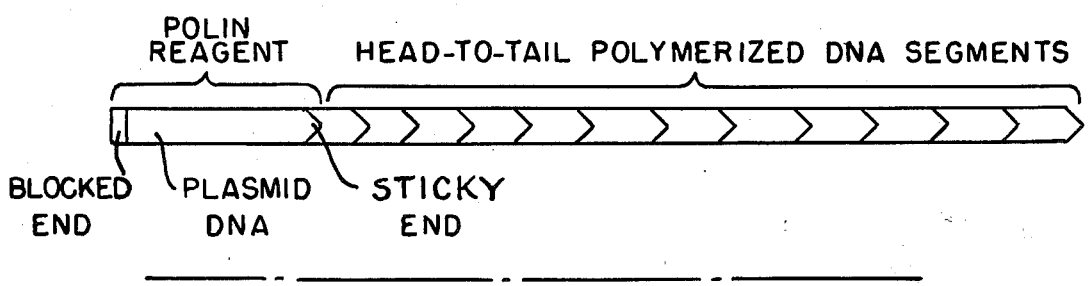

FIG. 8 illustrates the use of the POLIN reagent as the initiator reagent for joining the DNA segments of FIG. 4 to the plasmid DNA in head-to-tail conformation.

Figure 9:
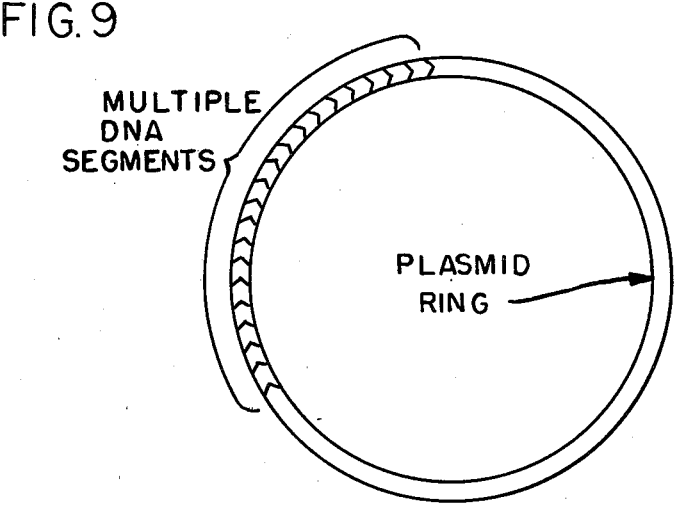

FIG. 9 illustrates the plasmid ring formed by circularizing the plasmid with the polymer of FIG. 8, thereby obtaining a genetic reagent for expression of protein from the multiple DNA segments.

Figure 1:
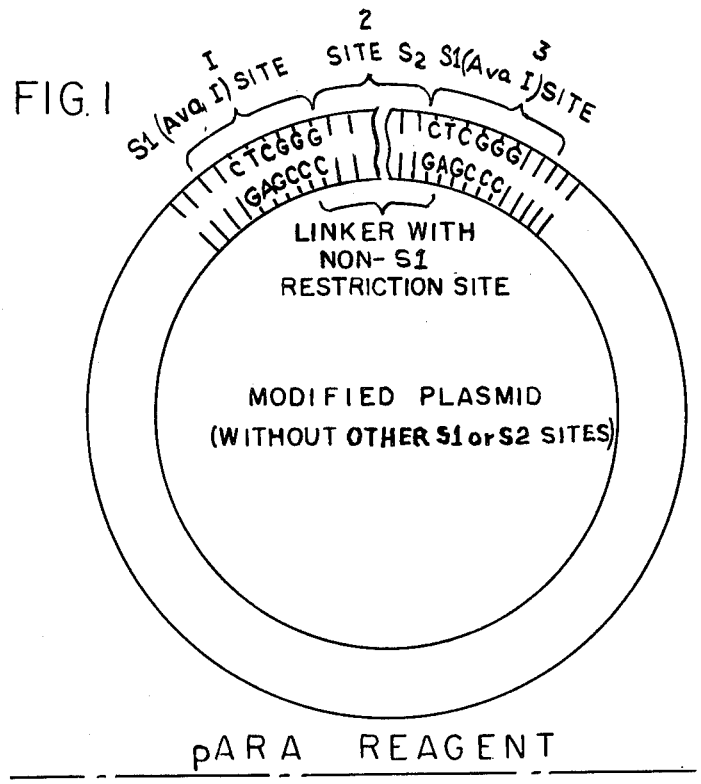
Figure 10:
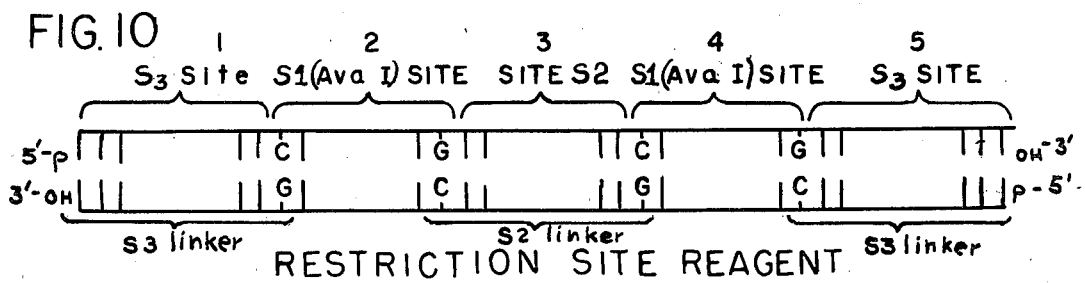

FIG. 10 illustrates the general structure of a restriction site reagent which can be used for inserting the three restriction site sequence of the pARA reagent shown in FIG. 1 into a different plasmid.

Figure 11:
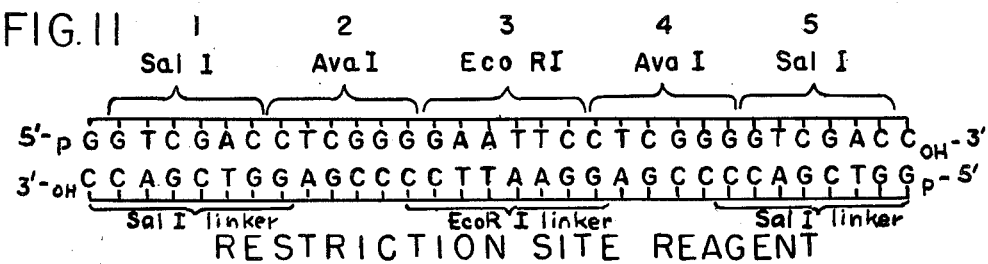

FIG. 11 represents the structure of a specific example of the restriction site reagent of FIG. 10, which includes a sequence of five restriction sites.

DETAILED DESCRIPTION

The techniques for manipulating bacterial plasmid rings to clone DNA segments and/or obtain expression of the protein directed by the recombinant DNA are known. For details of specific procedures, reference may be had to *Methods in Enzymology*, Vol. 65 (L. Grossman and K. Moldave, eds.) and Vol. 68 (R. Wu, ed.), published by the Academic Press, New York. The plasmid rings are double-stranded DNA and contain a number of different restriction enzyme cleavage sites which are cleavable with the appropriate restriction endonucleases. Plasmids which contain genetic information for resistance to antibacterial drugs (derivatives of R plasmids) are particularly useful for cloning and for genetic expression of cloned genes. Examples are the *Escherichia coli* plasmids which provide resistance to antibiotics such as penicillin, tetracycline, chloramphenicol, etc. Particularly advantageous are the plasmids derived from Col El, such as pBR322 and pMB9. However, many other plasmids can be used for the purpose of this invention, including pACYC184, pBR325, pCR1, and pBR313.

For example, the plasmid pBR322 contains a single Ava I site and a single EcoR I site. However, the presence of the EcoR I site is not essential, and in fact, it is desirable to eliminate this site if an EcoR I linker is to be used in preparing the pARA reagent of this invention. Further, if the plasmid ring contains no Ava I site, the three restriction site sequence of a pARA reagent can be formed outside of the plasmid and introduced therein. For purpose of illustration, however, the manipulation of the plasmid pBR322 to form the pARA reagent will be described.

Starting with the pBR322 plasmid, it is preferable to first remove the EcoR I restriction site. This is done by cleaving the plasmid with EcoR I endonuclease, reforming the cleaved ends to produce blunt ends, and then ligating the ends with a reagent such as T4 DNA ligase. The reformed plasmid is then free of an EcoR I site.

The EcoR I site-free plasmid is then cleaved with the Ava I endonuclease to provide rotationally non-equivalent Ava I sticky ends, as illustrated in FIG. 6. Non-symmetric Ava I cleavage sites are characterized by the sequence 5'-CTCGGG-3' and its complement 5'-CCCGAG-3', wherein C represents cytosine, T-thymine, G-guanine, and A-adenine. There is therefore one non-symmetric Ava I sequence in which the DNA ends produced by Ava I cleavage are rotationally non-equivalent. This site is distinguished from the two other symmetric Ava I sequences, which are 5'CCCGGG-3', and 5'-CTCGAG-3' and their respective complements. As the Ava I restriction site of pBR322 is represented by the non-symmetric sequence 5'-CTCGGG-3' and its complement, it is therefore usable for the purpose of the present invention.

The non-equivalent Ava I sticky ends of the cleaved EcoR I site-free pBR322 plasmid are then treated with the appropriate reagent to partially reform Ava I site groups at each end. For example, this can be accomplished by treatment with DNA polymerase I in the presence of dATP (2'-deoxyadenosine 5'-triphosphate), dCTP (2'-deoxycytidine 5'-triphosphate), dGTP (2'-deoxyguanosine 5'-triphosphate) and TTP (thymidine 5'-triphosphate). The filled in Ava I ends are then connected with a suitable restriction site-containing linker, using DNA ligase. The linker must contain a 5' cytosine and a 3' guanine on each strand to reconstitute the Ava I recognition sequence. A wide variety of suitable restriction site-providing linkers are available commercially. These contain from 4 to 10 base pairs. An EcoR I linker is a preferred example comprising the sequence 5'-GGAATTCC-3' on each strand. Other suitable molecular recombination linkers which would reconstitute the Ava I site are Hae III (5'-GGCC-3'); Hpa I (5'-GTTAAC-3'); Sal I (5'-GGTCGACC-3'); and Pst I (5'-GCTGCAGC-3'). All of these are available commercially, for example from Collaborative Research, Inc., Waltham, Mass. It will be understood from what has been said previously that preferably the linker is also selected to provide a restriction site different than any restriction site remaining in the plasmid. Therefore, if the plasmid contains a natural restriction site such as a Pst I site, and it is desired to use a Pst I linker, the Pst I site may be eliminated in a manner similar to that described for the EcoR I site of pBR322. To continue the specific illustration referred to above, the reformed Ava I ends of the split plasmid are connected by means of an EcoR I linker, using DNA ligase to connect the filled in Ava I ends to the ends of the EcoR I linker. The terminal base pairs of the linker complete the reconstitution of the flanking Ava I sites.

Figure 2:
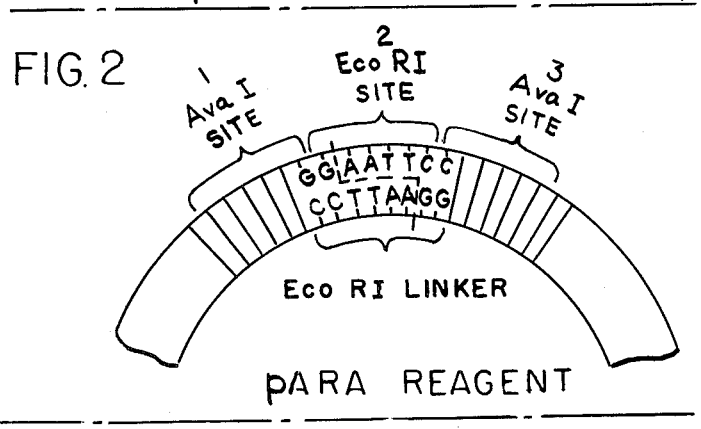

The circularized plasmid of modified construction thus obtained constitutes an example of the pARA reagent of this invention. As illustrated by FIG. 1, it is characterized by a sequence of three contiguous restriction sites in which the first and third sites are non-symmetric sites which upon cleavage yield sticky ends which are not rotationally equivalent, and the second site differs from the first and third sites. In this specific embodiment, the second site is an EcoR I site and the first and third sites are non-symmetric Ava I sites, as illustrated in FIGS. 1 and 2. As indicated in FIG. 1, the modified plasmid comprising the pARA reagent is preferably free of any S1 or S2 sites outside of the three site sequence.

Preparation of DNA Segment to be Polymerized

Any DNA segment, including those containing genetic information for protein expression, can be used with the pARA reagent described above. DNA segments containing from 50 to 2000 base pairs are particularly suitable. The modified plasmid ring comprising the pARA reagent preferably contains from about 3000 to 6000 base pairs, although plasmid rings ranging from 1000 to 1000,000 base pairs can be used.

Figure 3:
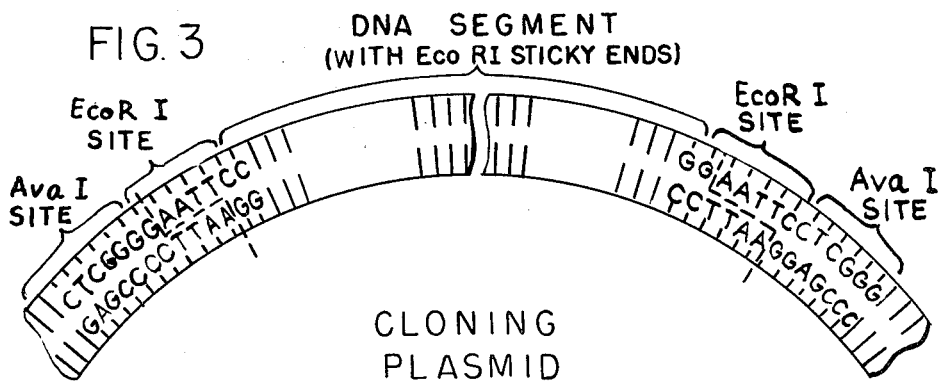
FIG. 3 illustrates the portion of the cloning plasmid containing the DNA segment chosen for multiplication which has been inserted between the Ava I sites at the EcoR I site.

The selected DNA segment (e.g., a gene) which will usually be obtained in a form with the usual 5'-P and 3'-OH end groups, is inserted between the non-symmetric S1 restriction sites of the pARA reagent after cleavage at the central S2 site. With reference to the specific pARA reagent shown in FIG. 2, this insertion process can be done in three ways, depending upon the nature of the DNA segment to be inserted. If the segment has EcoR I ends, it can be cloned directly into the EcoR I site of pARA. Alternatively, the ends of both the segment and the EcoR I-cut pARA can be made blunt, and the segment can be joined to pARA by blunt end ligation. Or EcoR I linker molecules could be used. The EcoR I linker would be used together with DNA ligase to provide EcoR I linker groups on each end of the DNA segment. The end groups are then cut with EcoR I enzyme to provide EcoR I sticky ends. The pARA reagent is similarly cut with the EcoR I enzyme to provide EcoR I sticky ends. In the presence of DNA ligase, the DNA segments with the EcoR I sticky ends are then inserted in the plasmid to close the plasmid ring. The resulting plasmid is illustrated in FIG. 3, the DNA segment having EcoR I groups at each end connecting to the Ava I sites.

The cloning plasmid is then transformed into E. coli and reproduced therein. The multiplied plasmids are then recovered from the bacterial cells, and the plasmid rings are cleaved with the Ava I restriction enzyme. If the DNA segment to be polymerized contains an internal Ava I site, the excision from pARA is done with a partial Ava I cut, and the full-length segment, with non-equivalent Ava I sticky ends, is recovered after gel electrophoresis. This produces the polymerizable DNA segments illustrated in FIG. 4. As will be noted, the cloned DNA terminates in non-equivalent Ava I sticky ends. It is the characteristic of these non-equivalent ends that they tend to attach to each other in only one configuration, which my be designated head-to-tail attachment.

Construction from pARA of the Polymerization Initiator POLIN

Figure 5:
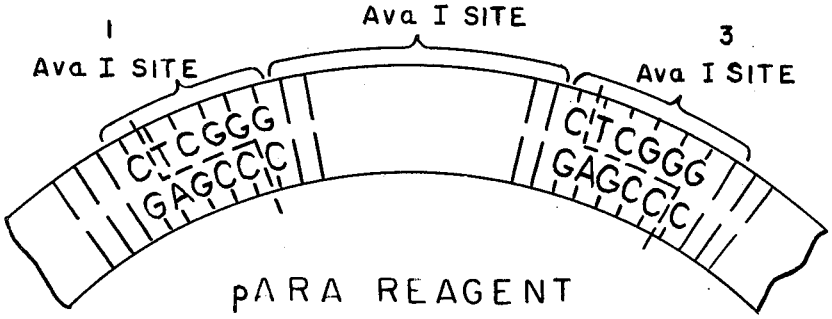
FIG. 5 is a further illustration of the restriction site sequence of the pARA reagent of FIG. 4 showing the Ava I site cleavage.

A polymerization initiator is prepared from the pARA reagent or directly from a plasmid containing a single non-symmetric restriction site. FIG. 5 illustrates in dotted lines the cleavage in the Ava I restriction sites which results in the sticky non-symmetric Ava I ends, as illustrated in FIG. 6. One of these ends, the "left" end, may be then filled in to provide a blunt or flush end, leaving the other end as an Ava I sticky end. For example, the blunt end may be formed with DNA polymerase I, dGTP, dCTP, and 2', 3'-dideoxyATP. This will produce both a blunt end and an end lacking a 3'-hydroxyl group, having instead a 3'-hydrogen. The blunt end will thereby provide a poor substrate for ligation, such as with T4 DNA ligase. The blunt end may thereby be considered as a "blocked" end. The ligation reactivity of the blunt end may also be blocked by removing the 5'-phosphate, to leave a 5'-hydroxyl group. For example, the blunt end may be formed with both dideoxyATP and alkaline phosphatase, to provide a blunt end which lacks both 5'-P and 3'-OH groups. Because the enzyme T4 DNA ligase will join two DNA termini together only if one terminus has a 5' phosphate and the other terminus has a 3' hydroxyl group, this blunt end is completely blocked for ligation. Although the sticky "right" end will then contain a 5'-PH group instead of a 5'-P group, that end will ligate by virtue of its remaining 3'-OH group with the polymerizable DNA segments having Ava I non-equivalent ends. The resulting polymerization initiator referred to herein as POLIN, is illustrated in FIG. 7.

Using the POLIN reagent of FIG. 7 and polymerizable DNA segments of FIG. 4, multiples of the DNA segments are then ligated to the plasmid DNA. More particularly, the DNA segments with the non-equivalent Ava I sticky ends are polymerized in the presence of the POLIN reagent and DNA ligase. For example, to the reaction mixture containing the POLIN reagent and DNA ligase, the polymerizable segments are gradually added and reaction is continued for a number of hours. The polymerizable DNA segments are added gradually to minimize the self-polymerization of the segments to circular form, thereby resulting in a loss of this reagent. For example the polymerization reaction can be conducted at a temperature of from 5° to 20° C., such as 16°, in the presence of DNA ligase, ATP, and a suitable buffer. The reaction is continued for several days with periodic addition of the DNA segments with the gradual growth of the head-to-tail polymerized DNA segments onto the POLIN reagent plasmid. This is illustrated diagramatically in FIG. 8, the blocked end and the sticky end of the POLIN reagent being respectively indicated, and the head-to-tail addition of the DNA segments being represented by the succession of outwardly pointed segments. The resulting product will be a mixture of ligated polymers of various lengths containing a range of DNA multiples, such as from 5 to 50 of the polymerized DNA segments. The resulting plasmid with the tandem repeats is then circularized. If the POLIN reagent shown in FIG. 7 is used, the sticky Ava I ends of the last DNA segments added are made blunt, e.g., with DNA polymerase I and deoxynucleotide triphosphates. The molecules are then ligated to circular form. If the blocked ends of the POLIN reagent lack both 5'-P and 3'-OH groups, the missing 5'-P groups can be put back on using ATP and the enzyme T4 polynucleotide kinase. The resulting blunt ends are then subject to ligation with DNA ligase to circularize the plasmids.

The resulting recombinant plasmids containing the multiples of the DNA segments are then transformed into E. coli with the resultant cloning of the plasmids. The cloned plasmids containing the multiple segments can then be recovered, or they can be retained in the bacterial cells, under conditions where the multiple DNA segments are expressed as the desired protein.

There is an important attribute of the invention when applied to increasing the expression of a cloned gene. That is that other genetic manipulations, e.g., changes in the RNA polymerase recognition sites of the gene, can be done prior to and independent of the DNA segment multiplication. Thus the normal sequence of events might be the cloning of the gene, manipulation of the structural and control regions to maximize expression, then polymerization of the DNA segment, which includes the entire functional unit, to further increase the yield of the gene product.

Where the cloned multiple segment plasmids are recovered by separation from the bacterial cells, individual DNA segments can be readily separated by cutting the plasmids with the restriction endonuclease corresponding to the restriction site linker introduced between the S1 sites of the pARA reagent, or with the S1 enzyme itself. For the preferred embodiment the S1 enzyme is Ava I and the linker (S2) enzyme is EcoR I. The EcoR I sites between each of the DNA segments would be cut with EcoR I enzyme to provide the separated segments with EcoR I sticky ends. This feature is important because of the potential usefulness of the multiple copy DNA segments as reagents in and of themselves. Reagents such as restriction site linkers, DNA sequencing primers, and molecular weight standards are sold by a number of companies, and these DNAs can be produced using the invention described here. Producing large quantities of novel DNAs, such as DNA segments controlling gene function, is also feasible. Excising multiple DNA copies from a plasmid for the production of such reagents is at least ten times as expensive when Ava I is used instead of EcoR I. Thus the use of restriction site linkers whose corresponding restriction enzyme is inexpensive compared to Ava I is a distinct advantage when the individual DNA segments are to be recovered in large quantity.

Restriction Site Reagent

A restriction site reagent can be prepared as illustrated in FIGS. 10 and 11 for transferring the three restriction site sequence of a pARA reagent to any plasmid. For the pARA reagent used above, the restriction site reagent may be prepared by cutting pARA with Ava I, to obtain an eight base pair DNA Segment (corresponding to the EcoR I linker molecule used to construct the pARA) with Ava I sticky ends. The ends of these fragments are then filled in using DNA polymerase I in the presence of dCTP, dGTP, dATP, and TTP. A linker containing a restriction site other than Ava I or EcoR I is then ligated to the blunt ends of the fragments using DNA ligase. The resulting restriction site reagent is illustrated in FIG. 10. As noted, it will contain five restriction sites, the second and fourth sites being Ava I, the first and fifth sites (designated S3 sites) being identical, and third site being a different site than any other in the reagent (designated S2). The S3 linkers are chosen such that their terminal base pairs reconstitute the non-symmetric S1 sites. In this example Sal I linkers are used because their terminal guanine-cytosine base pairs supply the final bases needed to reconstruct the Ava I sites. The resulting reagent is shown in FIG. 11, and has the total restriction site sequence Sal I-Ava I-EcoR I-Ava I-Sal I. This reagent can be inserted into any plasmid ring by standard methods, with or without the retention of the terminal Sal I sites, with the resulting introduction of the Ava I-EcoR I-Ava I sequence required of this type of pARA reagent.

Other procedures for transferring the restriction site sequence of a pARA reagent can be used. For example, an Ava I-EcoR I-Ava I sequence can be moved to another plasmid by cutting out the sequence with an enzyme such as Hpa II, and purifying the small fragment of about 100 base pairs containing the three site pARA. The fragment thus obtained could be ligated into any plasmid by standard procedures.

The preparation of genetic reagents in accordance with this invention and the use thereof is further illustrated by the following examples.

EXAMPLE I

A DNA segment 99 base pairs long containing one of the intron-exon boundaries of the rat prolactin gene was excised from a recombinant DNA plasmid (Gubbins, et al, *J. Biol. Chem.*, 255, 8655–8662, 1980) with the restriction enzymes Bgl II and EcoR I. The fragment was eluted from a 6% acrylamide gel (Bolivar and Backman, *Methods in Enzymology*, 68, 245, 1979) and the unpaired 5'-terminal ends were repaired with E. coli DNA polymerase I (15 pmol of 103 base pair fragment in 100 µM each dATP, dCTP, dGTP, and TTP, plus 20 units polymerase I, incubated for 10 minutes at 4° C). This blunt-ended fragment, called IX, was cloned into a plasmid (pARA) which was constructed for this experiment.

pARA was derived from the vector pBR322 in three steps: (1) pBR322 was cut with EcoR I, (which cuts the molecule only once at position 1), the unpaired 5' ends were made blunt using DNA polymerase I as described above, and the blunt ends were religated back together. This eliminated the EcoR I site by replacing the (top strand) sequence 5'-GAATTC-3' with the sequence 5'-GAATTAATTCC-3'. (2) The single Ava I site of the plasmid (5'-CTCGGG-3' at position 1424) was cut with Ava I, and the unpaired 5' ends were made blunt using DNA polymerase I. (3) An EcoR I "linker" molecule (a double-stranded octanucleotide in which both strands have the sequence 5'-GGAATTCC-3') was ligated between the blunt Ava I ends. This reconstituted the circular molecule with the sequence 5'-CTCGGGGAATTCCTCGGG-3' in place of the original Ava I site. The pARA reagent thus contained a single EcoR I site flanked on either side by identical Ava I sites. An important property of pARA is that any DNA segment cloned at the EcoR I site can be excised with Ava I, and the excised fragment will have non-symmetric sticky ends in the proper orientation for head-to-tail ligation. Because the tetracycline and ampicillin resistance genes of pBR322 are not altered by these manipulations, either of these drugs can be used for selection of appropriate clones.

To clone the 99 bp fragment into the pARA, pARA was cut with EcoR I and the 5'-terminal phosphates of the linear molecule were removed with bacterial alkaline phosphatase (Goodman and MacDonald, *Methods in Enzymology*, 68, 75, 1979). EcoR I linker molecules were ligated onto the IX fragment (10 pmol IX+270 pmol linkers+2 units T4 DNA ligase in 10 µl 66 mM Tris HCl, pH 7.6, 6.6 mM MgCl2, 10 mM dithiothreitol, 0.4 mM ATP, incubated 16 hours, 4° C.). The ligation products were treated with EcoR I to yield DNA with "sticky" EcoR I ends. These fragements were ligated into the EcoR I-cut and phosphatase-treated pARA (which could not be ligated to the circular form without an insert, because of the removal of the 5'-phosphates), again using T4 DNA ligase. The ligation mixture was used to transform E. coli strain HB101, and tetracycline-resistant colonies were selected (Bolivar and Backman, *Methods in Enzymology*, 68, 245, 1979). Plasmids prepared from these colonies were screened for the presence of one IX sequence, and about 3.5 mg of one such plasmid was purified (Kahn, et al, *Methods in Enzymology*, 68, 268, 1979). This plasmid was named pIX478.

About 3.0 mg of pIX478 was cleaved overnight with 50 units of Ava I at 37° C. and the IX fragment was purified by elution from an acrylamide gel. This IX fragment now contained non-symmetric Ava I-sticky ends, and will be referred to as the monomer fragment or as IX-Ava. Ligation of the monomer fragments to each other formed only direct tandem repeats, because of the asymmetry of the Ava I ends.

The monomer fragments were polymerized in vitro using a molecule named POLIN-A (for polymerization initiator), derived from pARA in the following way. pARA was cut with Ava I, and the "left" end of the linear molecule was filled in with DNA polymerase I and dGTP, dCTP, and 2', 3'-dideoxyATP. This end of the molecule was therefore both blunt and lacking a 3'-hydroxyl group, and was a poor substrate for T4 DNA ligase, while the other ("right") end was not repaired at all (because no TTP was added) and was therefore an excellent ligase substrate.

POLIN-A (2 pmol) and IX-Ava (10 pmol) were mixed with T4 DNA ligase (0.1 μl, equivalent to about 10 New England BioLabs units) in a total volume of 20 μl of 50 mM Tris-HCl, pH 7.8, 10 mM MgCl2, 20 mM dithiothreitol, 1 mM ATP, 50 ug/ml bovine serum albumin, and incubated at 16° C. Additional monomer (10 pmol) and ligase (10–50 units) were added once or twice a day for four (4) days. During this period the monomers were adding to the "right" end of POLIN-A, but the lengthening molecule could not circularize on itself because the "left" end was both blunt and lacked a 3'-hydroxyl group. After the ligation was complete, the "right" end was made blunt with DNA polymerase I and TTP, dCTP, and dGTP, and the molecule was circularized by ligation of the 3'-hydroxyl of the "right" end with the 5'-phosphate of the "left" end. (The circle was thus closed only with one strand, because the other strand lacked a 3'-hydroxyl and thus contained a nick. Although not the most efficient ligation, the procedure was staisfactory.) The final ligation mixture was used to transform E. coli HB101, and 15 resultant clones were screened for the number of monomers incorporated. The largest plasmid, named polypIX209, was prepared in quantity and characterized.

The number of monomers in polypIX209 was determined by a procedure analogous to Maxam-Gilbert DNA sequencing (Maxam and Gilbert, *Proc. Natl. Acad. Sci. U.S.A*, 74, 560, 1977). PolyIX209 DNA was cut with the enzymes BamH I and Sal I, which cleaved the circular molecule at positions 375 and 650 respectively, (the monomers were inserted at position 1424). Only the Sal I ends were labelled with $^{32}$P using DNA polymerase I, TTP, and [alpha-$^{32}$P] dCTP. The labelled DNA was then partially cut with Ava I, which cut between each monomer fragment, and the products were electrophoresed in an agarose gel. (Bolivar and Backman, *Methods in Enzymology*, 68, 245, 1979.) An autoradiograph of the desired gel showed a ladder of bands, which corresponded to Ava I fragments containing 0, 1, 2, 3, etc. monomers. Thirty-five bands were counted, showing that 34 monomers were present (since the smallest band corresponded to no monomers). All of the Ava I sites appeared to cut equally well, with the exception of the one between the twenty-second and twenty-third monomers, which cut much more poorly than the others. Some degradation of this Ava I site had evidently occurred during the ligation process.

The IX segment contained a site for the enzyme Hae III located 39 pb from one end and 84 bp from the other end. (The repeated IX sequence was now 123 base pairs long, owing to added Ava I and EcoR I sites on each end.) A ladder produced by a partial Hae III cut (using the same substrate as that used for the partial Ava I cut) showed a completely "regular" ladder. Since an inversion of any of the monomer fragments would have appeared as an irregularity in the spacing of the Hae III ladder, this experiment showed directly that all of the 34 monomers were in the same orientation.

The stability of the plasmid polypIX209 was tested in three ways:

(1) The plasmid was used to transform E. coli HB101, and eight transformants were screened for plasmid size. Of these eight, six appeared to be identical to polypIX209, one appeared to be somewhat larger (equivalent to a content of about 40 monomers), and one had two minor components which were smaller than the original plasmid.

(2) E. coli containing polypIX209 was cultured in broth under tetracycline selection for 57 generations, and individual clones were picked and screened for plasmid size by agarose gel electrophoresis. Of the 10 clones examined, 5 contained plasmids indistinquishable from polypIX209, 4 contained in addition to polypIX209 other plasmid bands in small to moderate amounts estimated to contain 30–38 monomers, and one clone had almost no polypIX209-size DNA, but contained instead a plasmid estimated to contain 25 monomers. (The stability of polypIX209 by these criteria is much greater than the plasmid constructed by Sadler, et al, which contained 12 repeats of the lac operator in a direct tandem orientation (Sadler, et al, Gene, 8, 279, 1980; Hardies, et al, *J. Biol. Chem.*, 254, 5527, 1979).

(3) Three large scale plasmid preparations (six mg each) yielded apparently homogeneous polypIX209 DNA.

It may be concluded, therefore, that polypIX209 contains exactly 34 tandem repeats of the IX monomer fragments, that all 34 monomers are present in the same orientation, and that the resulting plasmid is quite stable.

EXAMPLE 2

A POLIN molecule completely blocked at one end can be made by a modification used in Example 1. pARA is cut with Ava I, then treated with alkaline phosphatase to remove the 5'-phosphate groups from both ends. Then one end is filled with DNA polymerase I and dCTP, dGTP, and 2', 3'-dideoxyATP as in Example 1. This POLIN molecule, called POLIN-B, has one end which is blunt and lacks both 5'-P and 3'-OH groups, and is therefore not a substrate for T4 DNA ligase. The other end of POLIN-B, although it lacks a 5'-P group, is both sticky and has a 3'-OH group. Once the first monomer is added to this (by ligation to the 3'-OH of POLIN-B), further monomers can be added very easily.

To circularize the molecule after the addition of many monomers, it is necessary to restore the 5'-P group to the blocked end of the POLIN-B. This is done with the enzyme T4 polynucleotide kinase in the presence of adenosine 5'-triphosphate (ATP). After the other end of the molecule is made blunt with DNA polymerase I and TTP, dCTP, and dGTP, the two blunt ends are ligated together to reform the circular plasmid. The DNA is ready for transformation into E. coli as in Example 1.

POLIN-B is the preferred embodiment of the POLIN concept.

EXAMPLE 3

The plasmid pACYC184 is able to carry insertions approaching 50,000 base pairs with good stability. This plasmid is thus a good vector for carrying multiple copies of large DNA segments, e.g., genes encoding useful proteins.

To transfer the restriction site sequence Ava I-EcoR I-Ava I the plasmid pACYC184, pARA is cleaved with Ava I, and the ends of the small fragment are labelled and filled in using DNA polymerase I and TTP, dGTP, dATP, and [-$^{32}$P]dCTP. The small fragment is purified by acrylamide gel electrophoresis. Sal I linkers are ligated onto both ends of the fragment, follwed by Sal I cleavage and repair of the sticky Sal I ends with DNA polymerase I and deoxynucleotide triphosphates. The sequence of the blunt-ended fragment is now 5'-TCGACCTCGGGGAATTCCTCGGGGTCGA-3' and its complement. pACYC184 is cut with EcoR I (which cuts the plasmid ring only once), and the sticky EcoR I ends are filled in with DNA polymerase I and dATP and TTP. The flush-ended pARA-derived fragment is ligated between the two flush ends of pACYC184. Neither the original EcoR I site of pACYC184 nor the Sal I sites originally added to the small pARA-derived fragment remain. The EcoR I site (5'-GAATTC-3') of pACYC184 is replaced by the sequence 5'-GAATTTCGAG-Ava I-EcoR I-Ava I-GTCGAAATTC-3'. The resulting plasmid is thus a pARA-type reagent from which a POLIN-type reagent can be made.

We claim:

1. A genetic reagent for generating plasmids containing multiple copies of DNA segments, comprising a plasmid in circular form capable of being cloned in an appropriate bacterial host, said plasmid being characterized by containing a sequence, at least a part of said sequence being foreign DNA, the total sequence providing three contiguous restriction endonuclease cleavage sites in which the first and third sites are identical and in the same orientation, and the second site is different from the first and third sites, said first and third sites being comprised of non-symmetrically arranged base pairs, which when cleaved by a restriction endonuclease yield sticky ends which are not rotationally equivalent, said plasmid containing no other sites cleavable by the same restriction endonucleases as said three sites.

2. The genetic reagent of claim 1 in which said first and third restriction sites are non-symmetric Ava I sites.

3. The genetic reagent of claim 1 or claim 2 in which said plasmid is pBR322.

4. The genetic reagent of claim 1, claim 2, or claim 3 in which said second site is an EcoR I site.

5. A genetic reagent for generating plasmids containing multiple copies of DNA segments, comprising a pBR322 plasmid characterized by containing a sequence of three contiguous restriction sites in which the first and third sites are Ava I sites having non-symmetrically arranged base pairs, the second site is an EcoR I site, and said plasmid ring contains no other sites cleavable by either Ava I EcoR I restriction endonucleases.

* * * * *